(12) United States Patent
Prabhu et al.

(10) Patent No.: US 7,625,727 B2
(45) Date of Patent: Dec. 1, 2009

(54) **PROCESS FOR PRODUCING MYCOPHENOLIC ACID USING *PENICILLIUM ARENICOLA* BICC 7673**

(75) Inventors: Surekha Prabhu, Karnataka (IN); Pinakee Devi Sharma, Karnataka (IN); Sanjay Tiwari, Karnataka (IN); Ramakrishnan Melarkode, Karnataka (IN); Ramavana Gururaja, Karnataka (IN); Shrikumar Suryanarayan, Karnataka (IN)

(73) Assignee: Biocon Limited, Bangalore, Karnataka (IN)

( * ) Notice: Subject to any disclaimer, the term of this patent is extended or adjusted under 35 U.S.C. 154(b) by 0 days.

(21) Appl. No.: 11/576,712

(22) PCT Filed: Oct. 5, 2004

(86) PCT No.: PCT/IN2004/000309

§ 371 (c)(1),
(2), (4) Date: Dec. 5, 2007

(87) PCT Pub. No.: WO2006/038218

PCT Pub. Date: Apr. 13, 2006

(65) Prior Publication Data

US 2008/0227164 A1    Sep. 18, 2008

(51) Int. Cl.
*C12N 1/00* (2006.01)
*C12P 1/00* (2006.01)
*C12P 1/02* (2006.01)
*C12P 7/00* (2006.01)
*C12P 7/02* (2006.01)
*C12P 7/22* (2006.01)
*C12P 7/40* (2006.01)

(52) U.S. Cl. .................. 435/136; 435/41; 435/132; 435/155; 435/156; 435/171; 435/254.5; 435/256.3; 435/933

(58) Field of Classification Search .................. None
See application file for complete search history.

(56) References Cited

U.S. PATENT DOCUMENTS 4,178,213 A * 12/1979 Aldridge et al. ............. 435/126

FOREIGN PATENT DOCUMENTS

JP         60-78584         5/1985

OTHER PUBLICATIONS

Svendsen et al., A Chemotaxonomic Study of the Terverticilliate Penicillia Based on High Performance Liquid Chromatography of Secondary Metabolites, Mycological Research, vol. 98, Part 11, Nov. 1994.
Ozaki et al., 1987, Mycophenolic Acid Production by Drug-Resistant and Methionine or Glutamic-Acid Requiring Mutants of *Penicillium brevicompactum*, Agricultural and Biological Chemistry, Apr. 22, 1987.

* cited by examiner

*Primary Examiner*—David M. Naff
*Assistant Examiner*—Deborah K. Ware
(74) *Attorney, Agent, or Firm*—Allen, Dyer, Doppelt, Milbrath & Gilchrist, P.A.

(57) ABSTRACT

The present invention discloses the manufacture of MPA by fermentation under optimal fermentation parameters using a new strain of *Penicillium arenicola*.

2 Claims, No Drawings

PROCESS FOR PRODUCING MYCOPHENOLIC ACID USING *PENICILLIUM ARENICOLA* BICC 7673

FIELD OF THE INVENTION

The present invention relates to the production of Mycophenolic acid (MPA) using *Penicillium arenicola*.

BACKGROUND OF THE INVENTION

Mycophenolic acid (MPA) was initially isolated from a culture of a fungus belonging to the genus *Penicillium* and it is known that MPA is produced by many species belonging to the genus *Penicillium* such as *P. brevi-compactum, P. stoloniferum, P. scabrum, P. nagemi; P. szaferi, P. patri-mei; P. griscobrunneum, P. viridicatum* (Biochem. J. 26: 1442-1458, 1932) and *P. roqueforti* (Appl. Env. Microbiol. 37: 365-368, 1979).

MPA has a broad spectrum of activity like antitumor, antiviral, antipsoriatic, immunosuppressive and anti-inflammatory activity. It also exhibits antibacterial and antifungal activities. It is tolerable in large doses and has minimal side effects. It inhibits inosine monophosphate dehydrogenase, an important enzyme in de novo synthesis of inosine monophosphate, a precursor of purines. MPA also inhibits proliferation of lymphocytes that are responsible for immune response. This immuno repressory effect of mycophenolic acid has been important in treatment of organ rejection after organ transplant surgery.

Morpholino ester of mycophenolic acid is used as a pro-drug in pharmaceutical composition for treatment of rheumatoid arthritis, psoriasis and in prevention of tissue rejection in organ transplant patients.

*Penicillium brevi-compactum* strain has been used in submerged fermentation where it is reported to produce 2.4 mg MPA/ml at 27° C. in 6 days on shaking and 3.6 mg/ml at 27° C. in 14 days without shaking (U.S. Pat. No. 4,452,891). In solid substrate fermentation (SSF) it is reported to produce 3286 mg per Kg of wheat bran (Sadhukhan et al, J. Ind. Microbiol. Biotechnol. 22, 33-38, (1999). However there are no reports of *Penicillium arenicola* producing MPA.

SUMMARY OF THE INVENTION

The present invention related to the production of mycophenolic acid by *Penicillium arenicola* BICC 7673, its variants or mutants.

Accordingly the present invention provides
a) Production of MPA by *Penicillium arenicola*
b) Production of MPA by variants of *Penicillium arenicola*
c) Production of MPA by mutants of *Penicillium arenicola* and
d) A process for the production of MPA by fermentation using *Penicillium arenicola* and purification of MPA.

The process of present invention has the following advantages:
1. higher productivity by the new strain
2. economically attractive
3. industrially viable

DETAILED DESCRIPTION OF THE INVENTION

The first embodiment of the present invention is a new isolated and purified strain of *Penicillium arenicola* BICC 7673 producing MPA.

The second embodiment of the present invention is variants of the new strain.

The third embodiment of the present invention is mutants of the new strain. The mutants of the new strain can be obtained by classical mutagenesis or recombinant techniques.

The fourth embodiment of the invention is the use of the *Penicillium arenicola*, its variant or mutant for the production of MPA.

The fifth embodiment of the invention is the process of purification of MPA produced by *Penicillium arenicola*.

Isolation and Purification of the Strain

A fungal colony was isolated from soil sample procured from New Delhi, India. The soil isolation medium used was Czapex-Dox Agar with 0.5% yeast extract acidified with phosphoric acid to pH 4.0. Soil plate method designed by Warcup was followed. Soil plate was prepared by transferring a loopful of soil into a sterile petridish using a nichrome needle. 8 to 10 ml of the above soil isolation medium was added and swirled gently to disperse the soil particles. Ten such plates were made and incubated at 24 deg C. for 24 hrs. Tips of growing hyphae emerging from soil particles were teased out and transferred to Malt extract agar plates. The growth was followed up for ten days and isolates were purified by growing these fungal isolates on Malt extrat agar. This sample predominantly showed isolates of *Pencillium* species. One of the fungal isolates was accessioned into Biocon culture collection as BICC 7673.

Identification of the Strain

Colony habit: Colony on malt extract agar growing to a diameter of 24 mm at 25 deg C. in 7 days, conidial masses brown, reverse pale.

Morphology: Conidiophores smooth and thin walled, 4 µm diameter; rami present, metulae up to 12 µm, nonvesiculate and of equal length; phialides 8-10 µm long, flask shaped with short neck. Conidia nearly globose, up to 4 µm length, rough walled.

The strain is identified as *Penicillium arenicola*

Fermentation for the Production of MPA

The inoculum used for the seed can be spores or vegetative mycelium. The seed medium can be incubated at 22 to 30° C. for 40-55 hr. The production medium can be incubated at 22-30° C. for 148 to 300 hr. MPA is produced both on solid substrate and submerged fermentation.

Isolation and Purification of the Product

The product can be isolated and purified from the fermentation broth or substrate by any aqueous solution or combination or all of steps in any order described hereunder.

The aqueous phase containing the product can be extracted into water immiscible organic solvent. The water immiscible organic solvent is selected from one or more among ethyl acetate, butyl acetate, toluene, butanol etc. Optionally, an organic phase containing product can be partially concentrated using suitable techniques.

Accordingly the present invention provides a process for the manufacture and purification of MPA, characterized by—
(i) preparing seed inoculum of a strain of *Penicillium arenicola*
(ii) transferring the said seed inoculum to a production medium,
(iii) subjecting the said production medium to solid substrate or submerged fermentations,
(iv) feeding the substrate to be transformed in the said production medium at different intervals,
(v) extracting the product from the fermented biomass and separating MPA.

The process wherein the strain of *Penicillium arenicola* is *Penicillium arenicola* BICC 7673.

The process wherein the strain of *Penicillium arenicola* BICC 7673 is a strain deposited at MTCC (Microbial Type Culture Collection), Institute of Microbial Technology, Chandigarh, India, under accession number MTCC 5145.

The process wherein the said inoculum used for the seed is a spore suspension or a vegetative mycelium.

The process wherein the constituents of the said seed medium is selected from malt extract.

The process wherein the seed medium is incubated at 22 to 30 deg C. for 40 to 55 hours.

The process wherein the constituents of said production medium is selected from sucrose, tryptone, peptone and yeast extract.

The process wherein the said production medium is incubated at 22 to 30 deg C. for 120 to 240 hours.

The following examples further illustrate the invention, it being understood that the invention is not intended to be limited by the details disclosed therein.

EXAMPLE 1

One cryo vial containing *Penicillium arenicola* spores (BICC 7673) is aseptically transferred to a sterile 250 mL flask containing 40 mL of sterile medium containing 2% malt extract and grown at 28 deg C. shaker for period 48 hrs. 4 mL of this inoculum was taken and inoculated to 40 mL sterile production medium taken in 250 mL flasks and grown for 10 days at 28 deg C. The production medium composition is mentioned below.

Sucrose: 150 g/L
Tryptone: 18 g/L
Potassium chloride: 2 g/L
Potassium phosphate: 4 g/L
Potassium citrate: 2 g/L A total yield of 3.88 mg MPA/g end of fermentation broth was obtained.

EXAMPLE 2

One cryo vial containing *Penicillium arenicola* mycelial inoculum is taken and rest of the experiment-was done as mentioned in example 1. A total yield of 3.76 mg MPA/g end of fermentation broth was obtained.

EXAMPLE 3

One cryo vial containing *Penicillium arenicola* morphological variant is taken and rest of the experiment was done as mentioned in example 1. A total yield of 2.52 mg MPA/g end of fermentation broth was obtained.

EXAMPLE 4

One cryo vial containing *Penicillium arenicola* mutant is taken and rest of the experiment was done as mentioned in example 1. A total yield of 4.66 mg MPA/g end of fermentation broth was obtained.

EXAMPLE 5

30 L of the production medium as mentioned in example 1 was sterilized in a 50 L fermentor at 121-123 degree C. for 60 minutes. The same was inoculated with 10% v/v of well grown inoculum. At 162 hours, the fermenter was harvested and the product content (MPA) was estimated using HPLC analysis. A titre of 4.69 mg/g was obtained.

EXAMPLE 6

A single spore isolate of *Penicillium arenicola* was used. The organism was subcultured on a fresh MEA (Malt Extract Agar) slant and incubated at 26° C. After 5 days, the sporulated slant was suspended in 10 ml of water containing 0.01% tween 80. 500 µl of this spore suspension were spread on a fresh plate containing MEA. The plate was allowed to grow for 5 days. After 5 days the spores were scraped from the plate with a sterile loop and suspended in sterile distilled water. This spore suspension was used as the inoculum. 15 Kg of wheat bran was loaded on the bioreactor (plafractor U.S. Pat. No. 6,197,573) of approximately 22600 cm2 of plate area. The bioreactor was sterilized by sending steam simultaneously into the communicating and the noncommunicating channels to heat the bioreactor and its contents to a temperature of 121° C. for 90 minutes. The steam pressure was released and simultaneously sterile air was sent into the communicating channels while cooling water at approximately 25° C. was sent into the non-communicating channels.

The master seed for inoculation of culture was a $10^6$ spores/ml suspension of *Penicillium arenicola* in 14 L of sterilized distilled water containing 20% glycerol. This was used to inoculate the sterilized wheat bran so that the final moisture after inoculation was 60%. The inoculum was mixed thoroughly with the sterilized bran. Sterile airflow at a rate of 20 Lpm on the first day, 40 Lpm on second and third day and 20 Lpm on fourth and fifth day were sent into the bioreactor continuously. The temperature was controlled at 24° C. for all 5 days by conductive heating and cooling. The Mycophenolic acid production titres were assayed following extraction using the HPLC.

EXAMPLE 7

5 Kg. fermented wheat bran obtained from example 1 was then extracted by using 10 L of ethyl acetate and the extract was collected, analyzed and taken for further processing. The extraction efficiency of ethyl acetate was found to be 98%, as quantitated by HPLC.

EXAMPLE 8

The extract obtained from Example 7 was partially concentrated by distillation to remove ethyl acetate, leaving behind 3 L of residue. The residue was thrice extracted with equal volume of 10% NaOH solution in water. The aqueous extracts were combined. pH of the aqueous layer was adjusted to 3 to 3.5 using HCl. The aqueous solution was extracted with 3 L of ethyl acetate. This layer was first washed with water and then with brine solution. The ethyl acetate layer was concentrated and kept at 5 to 10° C. for 4 h for crystallization. The crystals were filtered, washed with ethyl acetate, and vacuum dried. The crystals thus obtained were of acceptable pharmaceutical grade.

We claim:

1. A biologically pure strain *Penicillium arenicola* BICC 7673 or mutants thereof having all of the identifying characteristics of said strain including production of mycophenolic acid (MPA).

2. A microbial process for the preparation of mycophenolic acid (MPA), comprising steps of:
   (i) preparing seed inoculum of a strain *Penicillium arenicola* BICC 7673 according to claim 1 using a soil isolating medium,
   (ii) processing the seed inoculum into a seed medium,
   (iii) subjecting the seed medium to solid substrate or submerged fermentation, and
   (iv) extracting and isolating MPA from the resulting fermented biomass using an aqueous solution and organic solvent.

* * * * *